United States Patent
Liou et al.

(10) Patent No.: US 10,307,448 B2
(45) Date of Patent: Jun. 4, 2019

(54) **METHOD FOR MANUFACTURING AN EXTRACT OF *RHINACANTHUS NASUTUS* (L.) KURZ**

(71) Applicant: HAN SHENG BIOTECH CO., LTD., Pingtung County (TW)

(72) Inventors: Shorong-Shii Liou, Pingtung County (TW); I-Min Liu, Pingtung County (TW); Chia-Ju Chang, Pingtung County (TW); Hou-Ru Ciou, Pingtung County (TW); Wei-Fan Chou, Pingtung County (TW)

(73) Assignee: HAN SHENG BIOTECH CO., LTD., Changjhih Township, Pingtung County (TW)

( * ) Notice: Subject to any disclaimer, the term of this patent is extended or adjusted under 35 U.S.C. 154(b) by 368 days.

(21) Appl. No.: 15/189,592

(22) Filed: Jun. 22, 2016

(65) Prior Publication Data

US 2016/0296575 A1 Oct. 13, 2016

Related U.S. Application Data

(62) Division of application No. 14/483,863, filed on Sep. 11, 2014, now abandoned.

(30) Foreign Application Priority Data

Jun. 20, 2014 (TW) .............................. 103121456 A

(51) Int. Cl.
*A61K 36/19* (2006.01)

(52) U.S. Cl.
CPC .......... *A61K 36/19* (2013.01); *A61K 2236/00* (2013.01); *A61K 2236/331* (2013.01); *A61K 2236/333* (2013.01)

(58) Field of Classification Search
None
See application file for complete search history.

(56) References Cited

FOREIGN PATENT DOCUMENTS

CN 102366504 A 3/2012

OTHER PUBLICATIONS

Brimson, et al., "*Rhinacanthus nasutus* Extracts Prevent Glutamate and Amyloid-β Neurotoxicity in HT-22 Mouse Hippocampal Cells: Possible Active Compounds Include Lupeol, Stigmasterol and β-Sitosterol", *Int. J. Mol. Sci.*, 2012 pp. 5074-5097, vol. 13.
Brimson et al., "*Rhinacanthus nasutus* Protects Cultured Neuronal Cells against Hypoxia Induced Cell Death", *Molecules*, 2011, pp. 6322-6338, vol. 16.
Tewtrakul et al., "Effects of rhinacanthins from *Rhinacanthus nasutus* on nitric oxide, prostaglandin $E_2$ and tumor necrosis factor-alpha releases using RAW264.7 macrophage cells", 2009, *Phytomedicine*, 16: 581-585.

*Primary Examiner* — Terry A McKelvey
*Assistant Examiner* — Catheryne Chen
(74) *Attorney, Agent, or Firm* — Muncy, Geissler, Olds & Lowe, P.C.

(57) ABSTRACT

The invention discloses a method for manufacturing an extract of *Rhinacanthus nasutus* (L.) Kurz in order to obtain the extract of *Rhinacanthus nasutus* (L.) Kurz with improved contents of active ingredients, wherein the method comprising the steps of: soaking a raw sample of *Rhinacanthus nasutus* (L.) Kurz with a processing reagent at 22 to 37° C. for 12 to 36 hours; boiling the soaked product at 1 atm, 95 to 105° C. for 15 minutes to 1 hour to obtain the processed sample of *Rhinacanthus nasutus* (L.) Kurz; extracting the processed sample of *Rhinacanthus nasutus* (L.) Kurz by 95% ethanol at 50° C.

9 Claims, 5 Drawing Sheets
(2 of 5 Drawing Sheet(s) Filed in Color)

METHOD FOR MANUFACTURING AN EXTRACT OF *RHINACANTHUS NASUTUS* (L.) KURZ

CROSS REFERENCE TO RELATED APPLICATIONS

This application is a divisional of co-pending U.S. patent application Ser. No. 14/483,863 filed on Sep. 11, 2014, for which priority is claimed under 35 U.S.C. § 120; and this application claims priority of Application No. 103121456 filed in TAIWAN on 20 Jun. 2014 under 35 U.S.C. § 119, the entire contents of all of which are hereby incorporated by reference.

BACKGROUND OF THE INVENTION

1. Field of the Invention

The present invention generally relates to a method for manufacturing an extract of *Rhinacanthus nasutus* (L.) Kurz in order to obtain the extract of *Rhinacanthus nasutus* (L.) Kurz with improved contents of active ingredients.

2. Description of the Related Art

*Rhinacanthus nasutus* (L.) Kurz, belonging to Acanthaceae, is a small erect, branched shrub and famous for its anti-oxidant ability. The ethanol extracts from leafs and roots protect cells from the detrimental effect of both glutamate and amyloid β protein, suggesting a possible use as a treatment for Alzheimer's disease.

Moreover, an active ingredient of *Rhinacanthus nasutus* (L.) Kurz, rhinacanthone (3,3-dimethyl-2,4-dihydrobenzo(h)chroment-5,6-dione), poses effect on inhibiting activity of human cervical cancer cell line, suggesting another possible use for treating cervical cancer. Several pharmacological studies also show that *Rhinacanthus nasutus* (L.) Kurz poses anti-fungi activity and ability of immunity regulation, and is useful to treat respiratory tract infection, pneumonia, sore throat, hepatitis, acne and hypertension.

Although *Rhinacanthus nasutus* (L.) Kurz shows several pharmacological effects on several diseases, extracts containing active ingredients are usually extracted from the unprocessed, raw sample of *Rhinacanthus nasutus* (L.) Kurz. However, the extract from the raw sample of *Rhinacanthus nasutus* (L.) Kurz shows a poor effect on treating liver cancer.

In light of this, it is necessary to provide a method for manufacturing an extract of *Rhinacanthus nasutus* (L.) Kurz for obtaining a processed sample of *Rhinacanthus nasutus* (L.) Kurz with improved activity against liver cancer.

SUMMARY OF THE INVENTION

It is therefore the objective of this invention to provide a method for manufacturing an extract of *Rhinacanthus nasutus* (L.) Kurz in order to obtain the extract of *Rhinacanthus nasutus* (L.) Kurz with improved contents of active ingredients.

It is another objective of this invention to provide a method for manufacturing an extract of *Rhinacanthus nasutus* (L.) Kurz in order to obtain the extract of *Rhinacanthus nasutus* (L.) Kurz with an improved activity against liver cancer.

One embodiment of the invention discloses a method for manufacturing an extract of *Rhinacanthus nasutus* (L.) Kurz comprising the steps of: soaking a raw sample of *Rhinacanthus nasutus* (L.) Kurz with a processing reagent at 22 to 37° C. for 12 to 36 hours; boiling the soaked product at 1 atm, 95 to 105° C. for 15 minutes to 1 hour to obtain a processed sample of *Rhinacanthus nasutus* (L.) Kurz; and extracting the processed sample of *Rhinacanthus nasutus* (L.) Kurz by 95% ethanol at 50° C.

In a preferred form shown, the method further comprises the step of: drying the processed sample of *Rhinacanthus nasutus* (L.) Kurz until the water content of the processed sample of *Rhinacanthus nasutus* (L.) Kurz is below 10%.

In a preferred form shown, the method further comprises the step of: before soaking the raw sample of *Rhinacanthus nasutus* (L.) Kurz with the processing reagent, removing impurities adhering on surfaces of the raw sample of *Rhinacanthus nasutus* (L.) Kurz.

In a preferred form shown, the processing reagent is wine or vinegar.

In a preferred form shown, 500 grains of the raw sample of *Rhinacanthus nasutus* (L.) Kurz is soaked with 400 mL of wine. Alternatively, 500 grams of the raw sample of *Rhinacanthus nasutus* (L.) Kurz is soaked with 150 mL of vinegar.

In a preferred form shown, the processing reagent is yellow wine or rice vinegar.

In a preferred form shown, the raw sample of *Rhinacanthus nasutus* (L.) Kurz is soaked with the processing reagent for 24 hours.

BRIEF DESCRIPTION OF THE DRAWINGS

The patent or application file contains at least one drawing executed in color. Copies of this patent or patent application publication with color drawings will be provided by the Office upon request and payment of the necessary fee.

The present invention will become more fully understood from the detailed description given hereinafter and the accompanying drawings which are given by way of illustration only, and thus are not limitative of the present invention, and wherein.

Figure 1A:
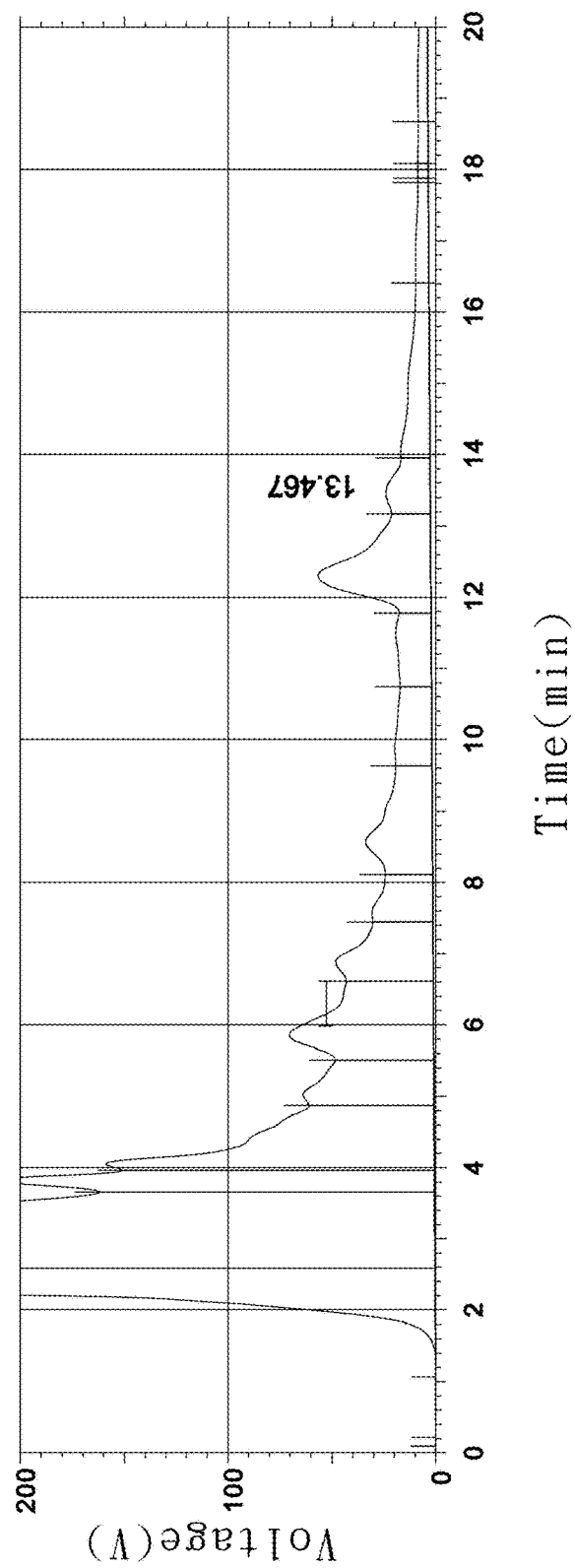
FIG. 1*a* depicts content of β-sitosterol of group A1 using HPLC analysis.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A method of processing *Rhinacanthus nasutus* (L.) Kurz according to the present invention comprises the steps of: soaking a raw sample of *Rhinacanthus nasutus* (L.) Kurz with a processing reagent at 22 to 37° C. for 12 to 36 hours; and boiling the soaked product at 1 atm (760 torr), 95 to 105°

C. for 15 minutes to 1 hour to obtain a processed sample of *Rhinacanthus nasutus* (L.) Kurz.

In the embodiment, the ground portion containing twigs and leafs is used as the raw sample. More particularly, the raw sample can be washed to remove impurities adhering on the surfaces of the raw sample, improving the processing process followed by.

The processing reagent is selected to be wine or vinegar. Preferably, the processing reagent is chose to be yellow wine or rice vinegar. In detail, in the first embodiment, 500 grains of the raw sample is washed to remove impurities of the surfaces, followed by soaking with 400 mL of yellow wine for 24 hours. Alternatively, in the second embodiment, after removing impurities on the surfaces, 500 grams of the raw sample is soaked with 150 mL of rice vinegar. The soaking time can be regulated as the amount of the processing reagent for totally absorbing the processing reagent during the soaking time.

After totally absorbing the processing reagent, the soaked product can be further boiled at 1 atm (760 torr), 95 to 105° C. for 15 minutes to 1 hour. If the boiling temperature is lower than 95° C., the efficiency in the following extraction will be poor. If the boiling temperature is higher than 105° C., the active ingredients will be possibly destroyed.

Preferably, the processed sample can be dried until the water content is below 10%. For example, the processed sample can be dried by freeze-drying, heated-drying or any methods well known in the art. In the embodiment, the processed sample is dried by freeze-drying.

In order to evaluate the method of the embodiment improves the actives ingredient-contents in the processed sample, and to further verify the processed sample of the embodiment poses improved ability of inhibition liver cancer proliferation, trials (A) to (C) are performed as following.

Trial (A): Contents of Active Ingredients

Referring to TABLE 1, 500 grains of the raw sample is soaked with yellow wine or rice vinegar, followed by boiling and drying, respectively (groups A1 and A2). 500 grains of the raw sample, or the dried sample of groups A1 or A2 blends with 1 liter of the 95% ethanol solution and the extraction is performed at 50° C. for 8 hours. The resulted products are further vacuum concentrated to remove the 95% ethanol solution to obtain the extracts of groups A0 to A2. Following trials with the extracts are carried on. The yield (%) shown in TABLE 1 is calculated as the following formula:

Yield (%)=(obtained amounts)/500×100%

TABLE 1

| Groups | Obtained amount (g) | Yield (%) |
| --- | --- | --- |
| A0 | 75.27 ± 5.81 | 15.05 ± 2.96 |
| A1 | 29.93 ± 3.23 | 5.98 ± 1.87 |
| A2 | 24.41 ± 4.64 | 4.88 ± 2.14 |

Moreover, β-sitosterol contents of the extracts shown in TABLE 1 further analyzed by HPLC are shown in TABLE 2.

TABLE 2

Figure 1B:
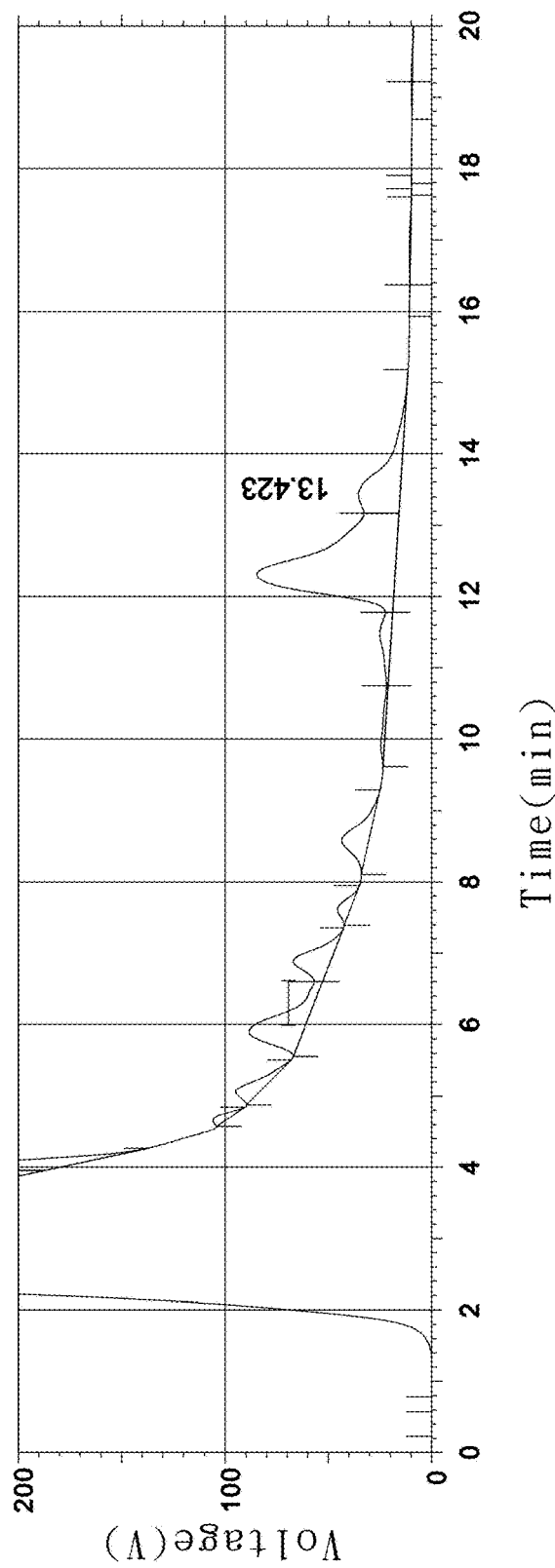
FIG. 1*b* depicts content of β-sitosterol of group A2 using HPLC analysis.
Figure 1C:
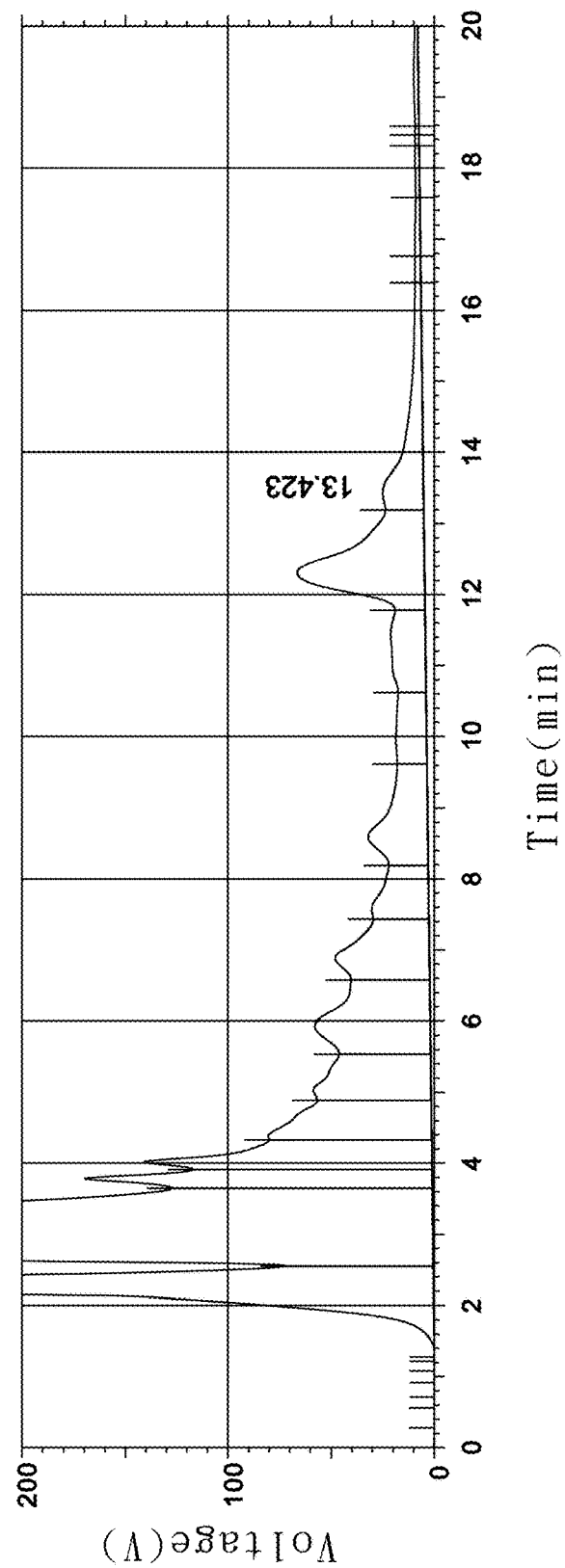
FIG. 1*c* depicts content of β-sitosterol of group A3 using HPLC analysis.

| Groups | β-sitosterol contents (mg/g) | HPLC results |
| --- | --- | --- |
| A0 | 0.58 ± 0.02 | FIG. 1a |
| A1 | 0.57 ± 0.01 | FIG. 1b |
| A2 | 1.02 ± 0.03 | FIG. 1c |

With respect to TABLE 2, group A2 has highest β-sitosterol content and is used in the following in vitro pharmacological study.

Trial (B): In Vitro Pharmacological Study

HepG2 (human liver cancer cell line, BCRC 60025) purchased from the Food Industry Research and Development Institute in Taiwan is used in trial (B). The HepG2 cells are cultured in DMEM medium (Dulbecco's Modified Eagle Medium) containing 10% FBS (purchased from Biological Industries, Kibbutz beit haemek), 2 mmol/L $_L$-glutamine (purchased from HyClone, USA), 1× nonessential amino acids (purchased from HyClone, USA), 100 μg/mL streptomycin and 100 U/mL penicillin (purchased from HyClone, USA). The HepG2 cells are incubated in an incubator with temperature of 37° C., $CO_2$ concentration of 5% and humidity of 95%. Medium used for culturing the HepG2 cells is renewed once in two days.

While subculturing, the HepG2 cells are centrifuged at 1,000 rpm for 5 minutes to remove supernatants, followed by mixing with fresh medium. The HepG2 cells preferably have a concentration of $1 \times 10^5$ to $1 \times 10^6$ cells/mL in 10 cm culturing dishes.

The culturing dishes 80 to 90% of bottom areas covered by the HepG2 cells are used in trial (B). Discolored medium is removed, 8 mL of PBS solution is used to wash the HepG2 cells and Trypsin/EDTA is added into the culturing dishes for 1 to 3 minutes. After the HepG2 cells dissociate with walls of the culturing dishes by slightly vortexing, the HepG2 cells are resuspended with prewarmed medium. The HepG2 cells are collected into centrifuge tubes, followed by centrifugation at 1,500 rpm for 10 minutes. Supernatants are removed and the HepG2 cells are resuspended in medium containing FBS. 20 μL of the HepG2 cells are collected, and 20 μL of trypan blue is added to the HepG2 cells for staining. The stained HepG2 cells are collected in cell counters, and numbers of the stained HepG2 cells are counted under microscope. Only the HepG2 cells with viability over 85% are suitable for the following experiments.

Concentrations of the HepG2 cells are adjusted to $1 \times 10^6$ cells/mL by medium containing FBS. 100 μL of the HepG2 cells with a concentration of $1 \times 10^5$ cells per are inoculated in a 96-well plate. The inoculated HepG2 cells are overnight cultured in an incubator with temperature of 37° C. and $CO_2$ concentration of 5%.

After culturing for 24 hours, 100 μL of the extracts shown in TABLE 3 (in a concentration of 1 mg/mL) are added into each well of the 96-well plate. The HepG2 cells treated with DMEM is used as the negative control (group B0). The HepG2 cells are overnight cultured in an incubator with temperature being 37° C. and $CO_2$ concentration being 5%.

TABLE 3

| Groups | Treatment | Survival Rate (%) |
| --- | --- | --- |
| B0 | DMEM | 100.00 ± 4.21 |
| B1 | Extract (group A0) | 58.85 ± 4.72 |
| B2 | Extract (group A1) | 50.37 ± 4.21 |
| B3 | Extract (group A2) | 46.34 ± 3.63 |

After culturing for 24 hours, medium is removed, and the HepG2 cells are washed by a PBS solution. 100 μL of CCK-8 containing-fresh medium is added into each well of the 96-well plate. The HepG2 cells react with CCK-8 for 2 hours in the incubator (37° C., 5% $CO_2$), followed by vortexing for 5 minutes. Absorbance of 450 nm of the tumor cells in each well is detected.

Survival rate of the HepG2 cells treated with the extracts shown in TABLE 4, while the survival rate is computed as followed:

Survival rate (%)=(Absorbance of a testing set/Absorbance of a control set)×100%

Referring to TABLE 3, HepG2 cells treated with the extracts of groups A1 and A2 have survival rates of 50.37±4.21% and 46.34±3.63%, respectively, which are obviously lower than HepG2 cells treated with the extract of group A0. That is, the extract of group A1 and A2 according to preferred teachings of the present invention poses a better effect on inhibiting liver cancer cell proliferation.

Trial (C): In Vivo Pharmacological Study

Specific-pathogen free Balb/C male mice (8 week-old, weight 20 to 25 g) purchased from The National Laboratory Animal Center (NLAC) are used in trial (C). The mice are housed in an animal room in the Experimental Animal Center of national Cheng Kung University with constant temperature of 25±1° C. where is kept on a 12-hours light and 12-hours dark cycle. The mice are housed and kept on free diet and water, which provided by the animal center of the Experimental Animal Center of national Cheng Kung University.

The HepG2 used in trial (C) are diluted to a concentration of $5 \times 10^6$ cells/mL by a saline solution. The diluted HepG2 cells are inoculated to the mice via axillary subcutaneous injection.

With respect to TABLE 4, the extracts of group A0, A1 and A2 is orally administrated to the mice in a dosage of 300, 500 mg per kilograms of the mice each time, and the oral administration is performed twice a day for 18 days, respectively (group C1 to C6). Group C0 is a control set without the extract (orally fed with RO water). Tumor burden is monitored by X-ray on day 8, 11, 15 and 18. Cancer-suppressing rates are recorded in TABLE 5. Symbol "*" and "**" indicates $p<0.05$ and $p<0.01$, respectively, compared with group C0.

TABLE 4

| Groups | Treatment | Tumor burden (mm³) | | | |
| --- | --- | --- | --- | --- | --- |
| | | Day 8 | Day 11 | Day 15 | Day 18 |
| C0 | RO water | 355.34 ± 42.39 | 622.72 ± 76.25 | 1194.45 ± 50.86 | 1695.10 ± 63.15 |
| C1 | Extract (group A0) 300 mg/kg | 315.51 ± 24.49 | 329.70 ± 37.55* | 750.11 ± 20.36* | 976.32 ± 27.73** |
| C2 | Extract (group A0) 500 mg/kg | 284.42 ± 14.60* | 228.41 ± 20.31** | 609.80 ± 23.54* | 1010.75 ± 26.77** |
| C3 | Extract (group A1) 300 mg/kg | 193.34 ± 12.16* | 306.96 ± 28.18** | 424.76 ± 25.50** | 605.11 ± 35.91** |
| C4 | Extract (group A1) 500 mg/kg | 173.75 ± 14.92** | 196.41 ± 17.96** | 371.52 ± 20.50** | 731.26 ± 28.32** |
| C5 | Extract (group A2) 300 mg/kg | 188.17 ± 18.14** | 196.32 ± 21.52** | 566.17 ± 31.91** | 816.84 ± 42.87** |
| C6 | Extract (group A2) 500 mg/kg | 172.68 ± 29.20** | 149.72 ± 10.74** | 328.13 ± 27.72** | 390.65 ± 38.70** |

TABLE 5

| Groups | Treatment | Cancer suppressing rate (%) | | | |
| --- | --- | --- | --- | --- | --- |
| | | Day 8 | Day 11 | Day 15 | Day 18 |
| C1 | Extract (group A0) 300 mg/kg | 11.26 ± 3.26 | 47.22 ± 5.13 | 37.18 ± 4.32 | 42.24 ± 6.13 |
| C2 | Extract (group A0) 500 mg/kg | 20.13 ± 4.83 | 63.34 ± 4.26 | 48.99 ± 5.26 | 40.36 ± 6.92 |
| C3 | Extract (group A1) 300 mg/kg | 45.59 ± 6.12 | 50.71 ± 6.48 | 60.65 ± 5.73 | 64.30 ± 7.14 |
| C4 | Extract (group A1) 500 mg/kg | 51.26 ± 6.98 | 68.48 ± 7.14 | 68.93 ± 9.12 | 56.87 ± 8.32 |
| C5 | Extract (group A2) 300 mg/kg | 47.04 ± 7.32 | 68.49 ± 8.32 | 53.43 ± 8.26 | 51.85 ± 9.26 |
| C6 | Extract (group A2) 500 mg/kg | 51.39 ± 6.87 | 76.04 ± 8.69 | 72.53 ± 7.84 | 76.99 ± 8.47 |

With reference to TABLEs 5 and 6, on day 8, mice of group C0 has a tumor burden of 355.54±42.39 mm³, while mice of groups C2, C4, C6 have tumor burden of 284.42±14.60 mm³, 173.75±14.92 mm³ and 172.68±29.20 mm³, respectively. Furthermore, compared to mice of group C0, cancer suppressing rate of mice of groups C2, C4 and C6 are 20.13±4.83%, 51.26±6.98% and 51.39±6.87%, respectively. That is, the extracts of groups A1 and A2 show better effect on inhibiting liver cancer progression. Moreover, on day 18, mice of group C6 has a tumor burden of 390.65±38.70 mm³ with a cancer suppressing rate of 76.99±8.47%. That is, administering the extract of group A2 in a dosage of 500 mg/day shows the best effect on inhibiting liver cancer progression.

On day 18, mice of groups C0 to C6 are sacrificed, and H&E staining is performed to verify the cancer progression status in mice of groups C0 to C6. The ratio between the necrosis region and the tumor region is recorded in TABLE 6.

TABLE 6

Figure 2A:
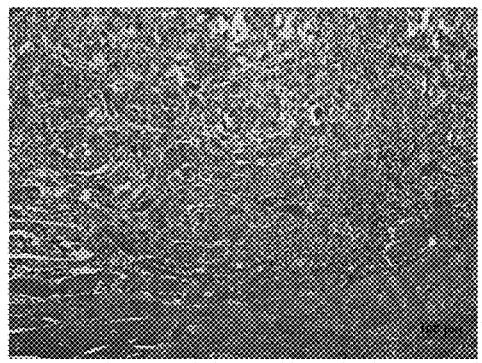
FIG. 2*a* depicts an H&E staining of group C0.
Figure 2B:
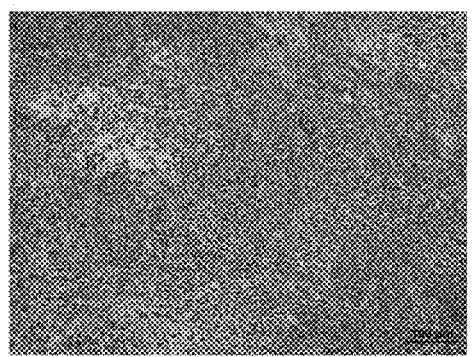
FIG. 2*b* depicts an H&E staining of group C1.
Figure 2C:
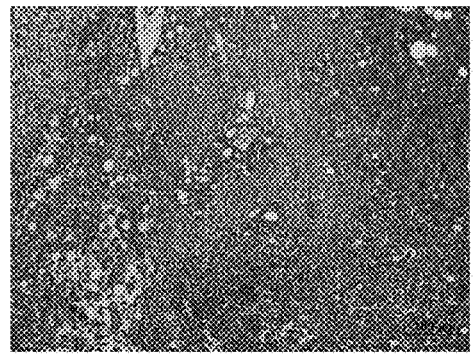
FIG. 2*c* depicts an H&E staining of group C2.
Figure 2D:
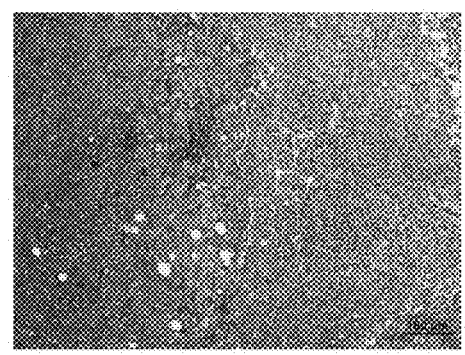
FIG. 2*d* depicts an H&E staining of group C3.
Figure 2E:
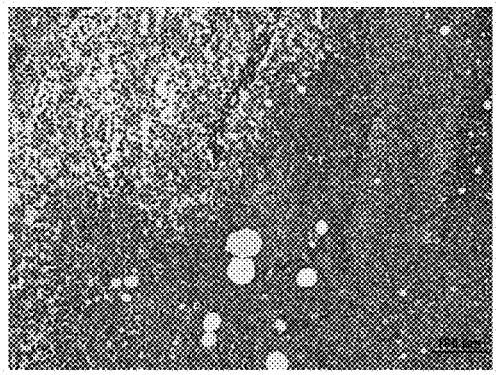
FIG. 2*e* depicts an H&E staining of group C4.
Figure 2F:
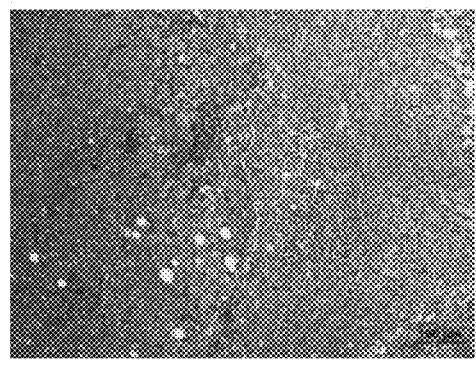
FIG. 2*f* depicts an H&E staining of group C5.
Figure 2G:
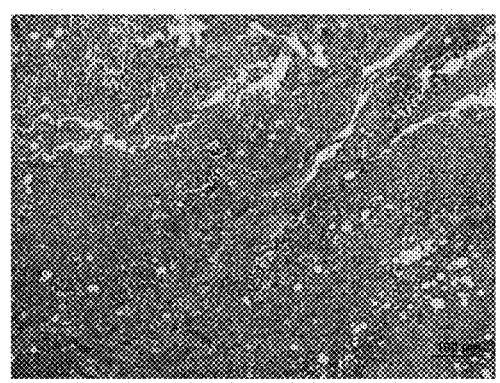
FIG. 2*g* depicts an H&E staining of group C6.

| Groups | Treatment | Ratio between the necrosis region and the tumor region | H&E staining |
| --- | --- | --- | --- |
| C0 | RO water | 1:9 | FIG. 2a |
| C1 | Extract (group A0) 300 mg/kg | 1:6 | FIG. 2b |
| C2 | Extract (group A0) 500 mg/kg | 1:4 | FIG. 2c |
| C3 | Extract (group A1) 300 mg/kg | 1:4 | FIG. 2d |
| C4 | Extract (group A1) 500 mg/kg | 1:2 | FIG. 2e |
| C5 | Extract (group A2) 300 mg/kg | 1:1 | FIG. 2f |
| C6 | Extract (group A2) 500 mg/kg | 2:1 | FIG. 2g |

Referring to TABLE 6, mice of group C0 has the highest tumor region distribution, while mice of group C6 has the lowest one. That is, administering the extract of group A2 in a dosage of 500 mg/kg of body weight once, twice a day for 18 days shows a better effect on preventing from liver cancer progression.

Accordingly, by performing the method for manufacturing an extract of *Rhinacanthus nasutus* (L.) Kurz, the obtaining extract of *Rhinacanthus nasutus* (L.) Kurz shows improved active ingredients for treating liver cancer. Therefore, the obtaining extract of *Rhinacanthus nasutus* (L.) Kurz can be used as an active substance against liver cancer, thereby effectively decreasing tumor burden and inhibiting liver cancer progression.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for manufacturing an extract of *Rhinacanthus nasutus* (L.) Kurz comprising the steps of:
    soaking a raw sample of *Rhinacanthus nasutus* (L.) Kurz with a processing reagent at 22 to 37° C. for 12 to 36 hours;
    boiling the soaked product at 1 atm, 95 to 105° C. for 15 minutes to 1 hour to obtain a processed sample of *Rhinacanthus nasutus* (L.) Kurz; and
    extracting the processed sample of *Rhinacanthus nasutus* (L.) Kurz by 95% ethanol at 50° C.

2. The method for manufacturing an extract of *Rhinacanthus nasutus* (L.) Kurz as claimed in claim 1, wherein the method further comprising the step of:
    drying the processed sample of *Rhinacanthus nasutus* (L.) Kurz until the water content of the processed sample of *Rhinacanthus nasutus* (L.) Kurz is below 10%.

3. The method for manufacturing an extract of *Rhinacanthus nasutus* (L.) Kurz as claimed in claim 1, wherein the method further comprising the step of:
    before soaking the raw sample of *Rhinacanthus nasutus* (L.) Kurz with the processing reagent, removing impurities adhering on surfaces of the raw sample of *Rhinacanthus nasutus* (L.) Kurz.

4. The method for manufacturing an extract of *Rhinacanthus nasutus* (L.) Kurz as claimed in claim 1, wherein the processing reagent is wine or vinegar.

5. The method for manufacturing an extract of *Rhinacanthus nasutus* (L.) Kurz as claimed in claim 4, wherein 500 grains of the raw sample of *Rhinacanthus nasutus* (L.) Kurz is soaked with 400 mL of wine.

6. The method for manufacturing an extract of *Rhinacanthus nasutus* (L.) Kurz as claimed in claim 4, wherein 500 grams of the raw sample of *Rhinacanthus nasutus* (L.) Kurz is soaked with 150 mL of vinegar.

7. The method for manufacturing an extract of *Rhinacanthus nasutus* (L.) Kurz as claimed in claim 4, wherein the processing reagent is yellow wine.

8. The method for manufacturing an extract of *Rhinacanthus nasutus* (L.) Kurz as claimed in claim 4, wherein the processing reagent is rice vinegar.

9. The method for manufacturing an extract of *Rhinacanthus nasutus* (L.) Kurz as claimed in claim 1, wherein the raw sample of *Rhinacanthus nasutus* (L.) Kurz is soaked with the processing reagent for 24 hours.

* * * * *